United States Patent [19]

Czaplewski et al.

[11] Patent Number: 5,440,069
[45] Date of Patent: Aug. 8, 1995

[54] DOMINANT ORANGE ALLELE IN PEPPER

[75] Inventors: Steven J. Czaplewski, Naples, Fla.; Herman E. J. Koning, Re DeLier, Netherlands

[73] Assignee: Sandoz Ltd., Basel, Switzerland

[21] Appl. No.: 284,717

[22] Filed: Aug. 2, 1994

Related U.S. Application Data

[63] Continuation of Ser. No. 102,397, Aug. 4, 1993, abandoned, which is a continuation of Ser. No. 801,985, Dec. 3, 1991, abandoned.

[51] Int. Cl.⁶ .......................... A01H 5/00; A01H 5/10; A01B 79/00
[52] U.S. Cl. ..................................... 800/200; 800/250; 800/255; 800/DIG. 41; 800/DIG. 71; 47/58
[58] Field of Search ....... 800/200, 250, 255, DIG. 41, 800/DIG. 71; Plt. 100; 47/58

[56] References Cited

PUBLICATIONS

Johnny's Selected Seeds Catalog. 1992, p. 43, Address: Foss Hill Road, Albion, Me. 04910-9731 Phone: (207) 437-4301.
Allard, R. W. 1960, Principles of Plant Breeding, (ch. 22) John Wiley & Sons, Inc. N.Y., N.Y. pp. 262-280.
Greenleaf, W. H. 1986 Pepper Breeding, (ch. 3) In Breeding Vegetable Crops. ed. M. J. Bassett, AVI Publishing Co., Westport, Ct. pp. 67-85; 90-97; 110-121.
Park Seed Flowers and Vegetables Catalog, 1991, (p. 112) Address: Cokesburg Road, Greenwood, S.C. 29647-0001, Phone (803) 223-7333.
Davies, et al. 1970, The Carotenoids of different colour varieties of *Capsicum annuum*. Phytochemistry. 9(4) 797–805.
Sigurbjornsson, B. 1983, Induced Mutatiors, In Crop Breeding (ch. 8) ed. D. R. Wood, American Society of Agronomy pp. 153-176 Madison, Wi.
Hurtado–Hernandez et al. 1985 "Inheritance of Mature Fruit Color in *Capsicum annum* L." *J. Heredity* 76:211–213.

*Primary Examiner*—David T. Fox
*Assistant Examiner*—Erich E. Veitenheimer
*Attorney, Agent, or Firm*—Lynn Marcus-Wyner; Allen E. Norris

[57] ABSTRACT

A novel dominant allele which imparts orange colored fruit in bell peppers has been identified. This allele can be used as part of a breeding program as an efficient way of controlling orange coloration. Line 434 and Hybrids NVH 3074 and 0366, are also described.

12 Claims, 5 Drawing Sheets

FIGURE #1

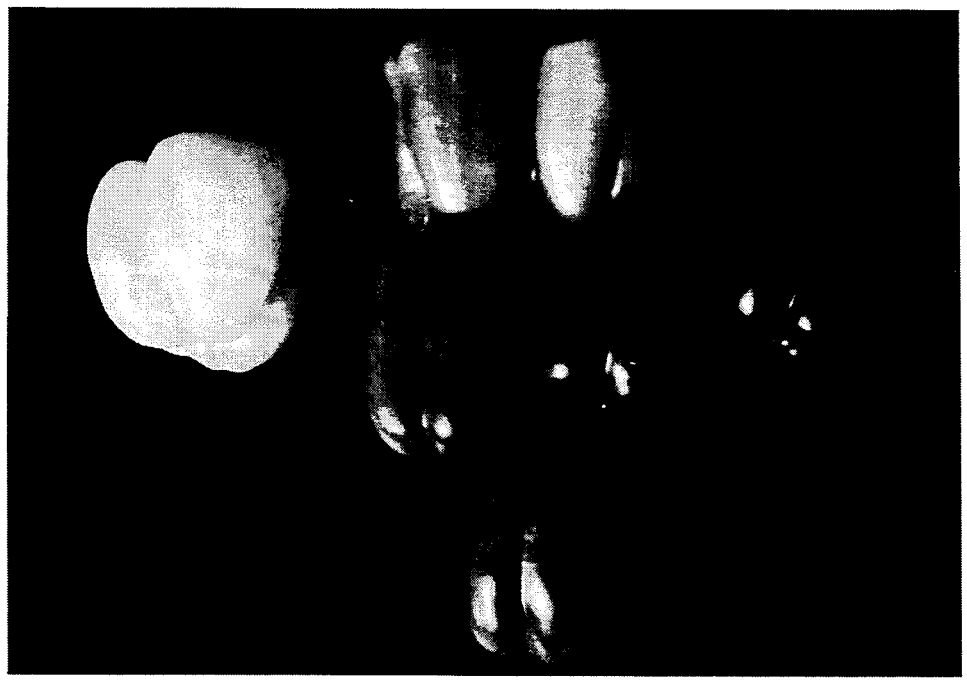
FIGURE #2

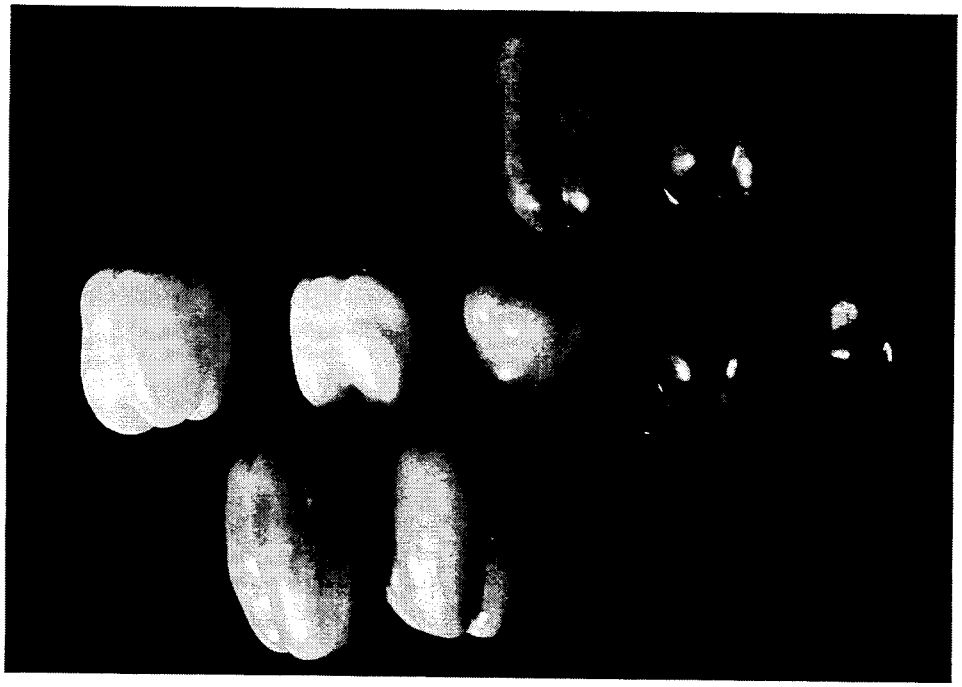
FIGURE #3

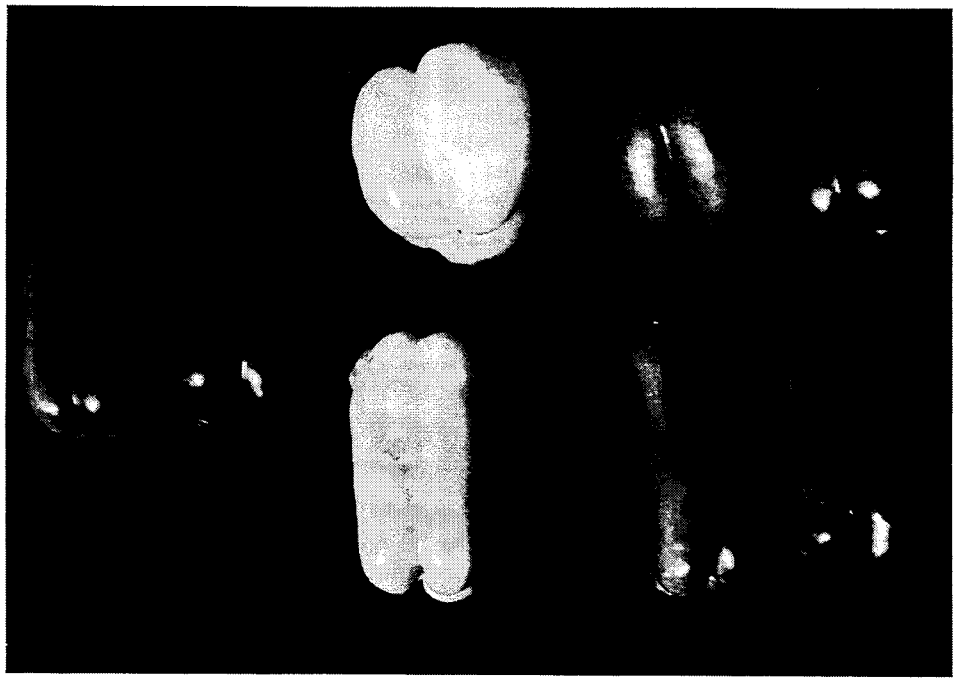
FIGURE #4

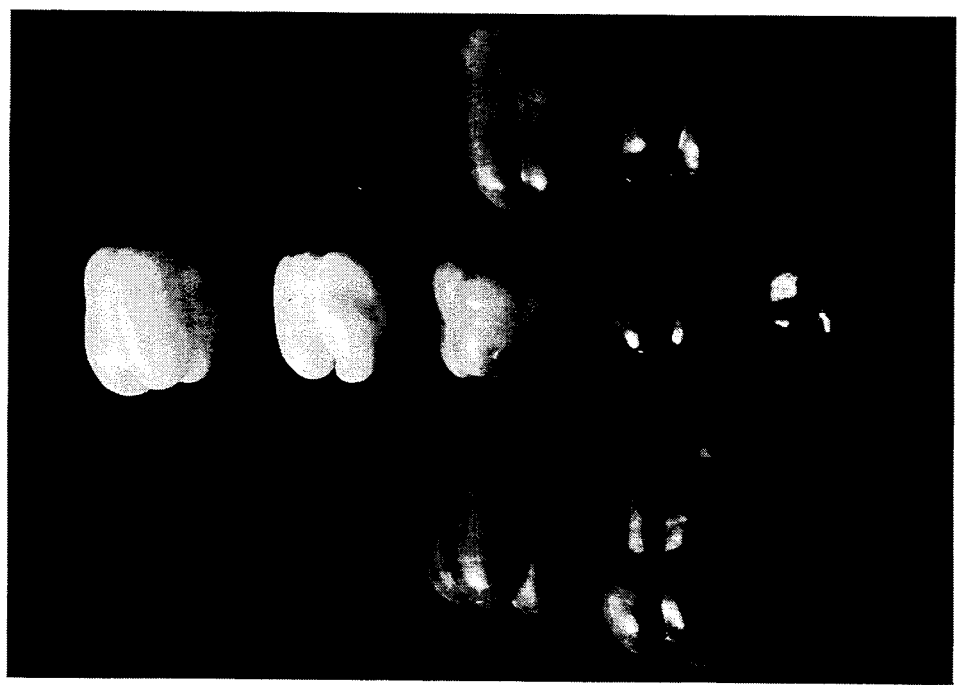
FIGURE #5

DOMINANT ORANGE ALLELE IN PEPPER

This is a CONTINUATION of application Ser. No. 08/102,397, filed Aug. 4, 1993, which is a CONTINUATION of application Ser. No. 07/801,985, filed Dec. 3, 1991, both now abandoned.

This invention relates to a novel allele which determines color in the bell pepper *Capsicum annuum L*. The novel allele is a dominant orange allele. Throughout this application and claims, colors referred to will pertain to mature fruit only.

BACKGROUND OF THE INVENTION

Orange color in bell peppers is known. Hernandez and Smith, 1985, *J. Heredity* 86:211–212, state that the color of mature fruit in bell peppers is governed by three genes y and $y^+$, $c_1$ and $c_1^+$, and $c_2$ and $c_2^+$. The F2 generation of the cross $(y^+c_1^+c_2^+)$ $(yc_1c_2)$ yields eight phenotypes:

| Genotype | Color | Munsell Color |
| --- | --- | --- |
| $y^+c_1^+c_2^+$ | Red (R) | 5 R 4/12 |
| $y^+c_1\ c_2^+$ | Light red (LR) | 2.5 R 4/12 |
| $y^+c_1^+c_2$ | Orange (O) | 10 R 6/12 |
| $y^+c_1\ c_2$ | Pale orange (PO) | 2.5 YR 7/12 |
| $y\ c_1^+c_2^+$ | Orange-yellow (OY) | 5 R 7/12 |
| $y\ c_1^+c_2$ | Pale orange-yellow (POY) | 10 YR 8/10 |
| $y\ c_1\ c_2^+$ | Lemon yellow (LY) | 5 Y 8.5/12 |
| $y\ c_1\ c_2$ | White (W) | 7.5 Y 9/4 |

The orange-yellow of Hernandez and Smith would be popularly identified as "yellow" by the consumer. However, to avoid confusion, throughout this specification and claims, the terminology of Hernandez and Smith will be used, and thus this colored pepper will be referred to as "orange-yellow". (A photograph illustrating this color appears in FIG. 3). Thus when one crosses an orange-yellow pepper line with one of the orange colored lines, the following results are seen (colors are expressed in Hernandez and Smith terminology):

| Parent #1 | Parent #2 | F1 | F2 |
| --- | --- | --- | --- |
| Pale Orange | Orange-Yellow | 100% Red | 27R: 9LR: 9O: 9OY: 3PO: 3POY: 3LY: 1W |
| Orange | Orange-Yellow | 100% Red | 9R: 3O: 3OY: 1LY |
| Light Red | Orange-Yellow | 100% Red | 9R: 3LR: 3OY: 1POY |

As can be seen from the above chart, one cannot produce an orange colored hybrid simply by crossing an orange colored line with a yellow line, as the F1 progeny are all red. It would be desirable to have an orange-colored pepper line, which when crossed to a yellow-colored pepper line, would produce orange-colored F1 peppers, rather than red.

DESCRIPTION OF THE INVENTION

This invention relates to a novel allele which controls orange color in bell pepper fruits. This allele is dominant; i.e. when crossed with an "orange-yellow" plant, the F1's will be orange-colored, not "orange-yellow" or red.

As used throughout the specification and claims, the term "orange colored" is intended to be a generic one, encompassing the range of colors from light red through orange and pale orange (using the terminology of Hernandez and Smith, supra). Using the Munsell system, "orange colored" ranges from 2.5R 4/12 (for light red) through 10R 6/12, and can extend to colors as light as 2.5 YR 7/12 (for pale orange). To avoid confusion with the generic designation, the term "medium orange" will be used to describe the color which Hernandez and Smith designated merely as "orange."

DESCRIPTION OF THE DRAWINGS

The file of this patent contains at least one drawing executed in color. Copies of this patent with color drawings will be provided by the Patent Trademark Office upon request and payments of the necessary fee.

FIG. 1 is a color photograph of orange pepper line 434.

FIG. 2 is a color photograph of five bell pepper lines. On the left is a "yellow-orange" fruit, and on the right is a "red" fruit. In the middle are three orange-colored lines, The top two orange-colored fruit are from the line 'Ariane'. The middle two orange-colored fruit are from the line '434'. The bottom one is fruit from the line 'Dorz'.

FIG. 3 is a color photograph illustrating various shades of color in bell pepper fruit. Across the middle are five fruits, corresponding to the following colors (left to right): "orange-yellow", "pale orange", "medium orange", "light red", and "red". On the top is line '434' whose color is between "medium orange" and "light red". On the bottom is the line 'Ariane' whose color is between "orange-yellow" and "medium orange".

FIG. 4 is a color photograph showing (left to right) two fruit of line '434'. In the middle are two "orange-yellow" inbred lines; at the top is a blocky yellow pepper, and at the bottom is an elongated yellow pepper. The progeny of the cross of '434' with each parent is shown at the right.

FIG. 5 is a color photograph illustrating the various shades of pepper fruit (as in FIG. 3). Line '434' is on the top, and hybrids of FIG. 4 are on the bottom. Hybrids are of essentially the same color as '434'.

DETAILED DESCRIPTION OF THE INVENTION

Pepper line 'Novi' (a commercially available hybrid) normally has red mature fruit. However, a spontaneous orange-colored mutant was discovered during the course of inbreeding 'Novi', and the line '434' was developed from the mutant plant. It was subsequently discovered that line '434' has an orange allele that was dominant. This dominant allele for orange color imparts a mature fruit color which is between "medium orange" and "light red", and is illustrated in FIG. 1. According to the Munsell color system, this "orange" color is described as 7.5R 5/12 to 7.5R 5/14. In addition, the line '434' differs form the original parent hybrid 'Novi' in that the leaves and fruit of '434' are larger and the plant is more vigorous.

Pepper line '434' is a proprietary pepper inbred line, and of this date it is not the parent of any publicly available pepper hybrids. Line '434', being an inbred, can be propagated through self-pollination. Line '434' may be used as a parent (either male or female) along with a second pepper in making hybrid peppers, and it is within the skill of the ordinary artisan to determine appropriate hybridization partners. If the second pepper has "orange-yellow" colored fruit, then the hybrid will have orange colored fruit, and this orange-colored fruit is substantially the same shade of orange as is present in line "434", i.e. between "medium orange" and "light red".

In addition, line '434' may be used as a source of the dominant orange allele and this allele can be transferred using known breeding protocols (such as backcrossing) to other pepper breeding lines. These newly-derived lines (now containing the dominant orange allele) can be used to produce commercially desirable orange peppers, which apart from the dominant orange trait, share very little, if any germplasm with line '434'.

The dominant orange allele imparts an orange color to mature fruit which is illustrated in FIG. 1. This may be contrasted with other mature fruit colors as shown in FIG. 2. On the left is a "orange-yellow" fruit, and on the right is a "red" fruit. In the middle are three different orange-colored lines. The top two orange fruit are from the commercially available line 'Ariane'. The middle two orange fruit are from the line '434' The bottom one is fruit from an experimental line 'Dorz'.

FIG. 3 is a color photograph illustrating various shades of color in bell pepper fruit. Across the middle are five fruits, corresponding to the following colors (left to right): "orange-yellow", "pale orange", "medium orange", "light red", and "red". On the top is line '434' whose color is between "medium orange" and "light red". On the bottom is the line 'Ariane' whose color is between "orange-yellow" and "medium orange".

Two particularly interesting hybrids which have been developed having the dominant orange allele are NVH 3074 and 0366, both of which comprise another aspect of this invention, and are described further in the Examples, below.

Seeds of hybrid NVH 3074 were deposited under the Budapest Treaty with the American Type Culture Collection, 12301 Parklawn Drive, Rockville, Md. and received accession number ATCC 75141 on Dec. 2, 1991.

The following Examples better illustrate the invention.

EXAMPLE 1

Description of Line '434'

The following data were gathered from line '434' in 1991.

MARKET MATURITY:
  Days from transplanting until mature green stage 115
  Days from direct seed until mature green stage 182
  Days from transplanting until mature orange stage 125
  Days from direct seed until mature orange stage 192
PLANT CHARACTERISTICS:
  Habit Compact
  Height 40 cm
  Width 38 cm
  Length of 3rd internode 30 mm
  Basal branches Few (2-3)
  Branch flexibility Rigid (as in 'Yolo Wonder L')
LEAVES:
  Foliage color Medium green
  Leaf and stem pubescence Absent (as in 'Yolo Wonder L')
  Mature shape Elliptic
  Mature size Medium (as in 'Anaheim Chili')
FLOWER:
  Calyx lobe number 6
  Petal number 6
  Corolla color White
  Corolla throat markings None
  Anther color Yellow
  Style length Same as stamen
  Flower number per leaf axil One
  Self-incompatibility Absent
  Cytoplasmic male sterility Absent
FRUIT
  Group Bell (as in 'Yolo Wonder L')
  Pungency Sweet (as in 'Yolo Wonder L')
  Immature color Medium green (as in 'Long Thin Cayenne')
  Mature color Orange
  Surface smoothness Smooth (as in 'Yolo Wonder L')
  Calyx shape Saucer-shaped
  Position Pendant (as in 'Jalapeno')
  Base shape Cupped (as in 'Yolo Wonder L')
  Apex shape Blunt (as in 'Yolo Wonder L')
  Flesh thickness Thick (as in 'Yolo Wonder L')
  Length 7 cm
  Diameter of Fruit at calyx attachment 75 mm
  Weight per fruit 154 g
  Fruit shape Bell (as in 'Yolo Wonder L')
  Fruit set Concentrated
  Number of locules 3-4
  Pedicel length Short (as in 'Yolo Wonder L')
  Pedicel shape Curved
  Pedicel thickness Slender (as in 'Cayenne')
SEED
  Seed color Yellow
  Weight 9.2 g/1000 seeds
ANTHOCYANIN
  Leaf Absent
  Fruit Absent
  Stem Absent
  Node Absent
  Calyx Absent
  Pedicel Absent
  Seedling hypocotyl Absent
DISEASE REACTION
  Pepper mottle virus Susceptible
  Potato Y virus Susceptible
  Tobacco etch virus Susceptible
  Tobacco Mosaic Virus Resistant '434' most closely resembles the known variety 'Ariane' in terms of maturity, plant habit, and mature fruit color (although its fruit color genotype is different than 'Ariane'). It most closely resembles known variety 'Yolo Wonder L' in terms of leaf color, leaf shape, fruit shape, immature fruit color and pungency. Mature fruit color ranged from 7.5R 5/12 to 7.52 5/14.

Seeds of inbred pepper line '434' were deposited under the Bundapest Treaty with the American Type Culture Collection, 12301 Parklawn Drive, Rockville Md. 20852 on Dec. 14, 1994 and have received accession number ATCC 75975.

EXAMPLE 2

Line '434' was crossed with a proprietary blocky yellow pepper inbred line 90-3061. The result was an orange blocky pepper, designated hybrid NVH 3074, which is shown at the top right of FIG. 4. As can be seen in FIG. 5, the hybrid orange blocky pepper has the substantially the same orange color as line '434' Other characteristics of NVH 3074 are presented below.
MARKET MATURITY:
  Days from transplanting to mature green stage 104

Days from direct seed until mature green stage 178
Days from transplanting until mature orange stage 116
Days from direct seed until mature orange stage 190
PLANT CHARACTERISTICS:
  Habit Spreading
  Height 50 cm
  Width 51 cm
  Length of third internode 25 mm
  Basal branches Few (2–3)
  Branch flexibility Rigid (as in 'Yolo Wonder L')
LEAVES:
  Foliage color Dark green
  Leaf and stem pubescence Absent (as in 'Yolo Wonder L')
  Mature shape Elliptic
  Mature size Medium (as in 'Anaheim Chili')
FLOWER:
  Calyx lobe number 7
  Petal number 6
  Corolla color White
  Corolla throat markings None
  Anther color Purple
  Style length Same as stamen
  Flower number per leaf axil One
  Self-incompatibility Absent
  Cytoplasmic male sterility Absent
FRUIT:
  Group Bell (as in 'Yolo Wonder L')
  Pungency Sweet (as in 'Yolo Wonder L')
  Immature color Medium green (as in 'Long Thin Cayenne')
  Mature color Orange
  Surface smoothness Smooth (as in 'Yolo Wonder L')
  Calyx shape Saucer-shaped
  Position Pendant (as in 'Jalapeno')
  Base shape Cupped (as in 'Yolo Wonder L')
  Apex shape Blunt (as in 'Yolo Wonder L')
  Flesh thickness Thick (as in 'Yolo Wonder L')
  Length 9 cm
  Diameter of fruit at calyx attachment 90 mm
  Weight per fruit 225 g
  Fruit shape Bell (as in 'Yolo Wonder L')
  Fruit set Scattered
  Number of locules 3–4
  Pedicel length Short (as in 'Yolo Wonder L')
  Pedicel shape Curved
  Pedicel thickness Thick (as in 'Yolo Wonder L')
SEED:
  Color Yellow
  Weight 6.9 g/1000 seeds
ANTHOCYANIN:
  Leaf Absent
  Fruit Absent
  Stem Absent
  Node Present
  Calyx Absent
  Pedicel Absent
  Seedling hypocotyl Present
DISEASE REACTION
  Pepper mottle virus Susceptible
  Potato Y virus Susceptible
  Tobacco etch virus Susceptible
  Tobacco mosaic virus Resistant Hybrid NVH 3074 most closely resembles the known variety 'Yolo Wonder L' in terms of maturity, plant habit, leaf color, fruit shape, immature fruit color, and pungency. It is most similar to 'Verdel' in terms of leaf shape, and closest to 'Ariane' in terms of mature fruit color. According to the Munsell System, NVH 3074 mature fruit color ranges from 10R 5/12 to 10R 5/16.

EXAMPLE 3

Line '434' was crossed with an elongate yellow pepper, proprietary line 90-3069. The result was an elongate orange pepper, designated hybrid 0366, as shown at the bottom right of FIG. 4. As can be seen in FIG. 5, the hybrid elongate orange pepper has substantially the same orange color as line '434' Hybrid 0366 has the following additional characteristics:
MARKET MATURITY:
  Days from transplanting to mature green stage 104
  Days from direct seed until mature green stage 178
  Days from transplanting until mature orange stage 115
  Days from direct seed until mature orange stage 189
PLANT CHARACTERISTICS:
  Habit Spreading
  Height 50 cm
  Width 54 cm
  Length of third internode 26 mm
  Branch flexibility Rigid (as in 'Yolo Wonder L')
LEAVES:
  Foliage color Dark green
  Leaf and stem pubescence Absent (as in 'Yolo Wonder L')
  Mature shape Elliptic
  Mature size Large (as in 'Yolo Wonder L')
FLOWER:
  Calyx lobe number 6
  Petal number 6
  Corolla color White
  Corolla throat markings None
  Anther color Purple
  Style length Same as stamen
  Flower number per leaf axil One
  Self-incompatibility Absent
  Cytoplasmic male sterility Absent
FRUIT:
  Group Bell (as in 'Yolo Wonder L')
  Pungency Sweet (as in 'Yolo Wonder L')
  Immature color Dark green (as in 'Yolo Wonder L')
  Mature color Orange
  Surface smoothness Smooth (as in 'Yolo Wonder L')
  Calyx shape Saucer-shaped
  Position Pendant (as in 'Jalapeno')
  Base shape Cupped (as in 'Yolo Wonder L')
  Apex shape Blunt (as in 'Yolo Wonder L')
  Flesh thickness Thick (as in 'Yolo Wonder L')
  Length 16 cm
  Diameter of fruit at calyx attachment 85 mm
  Weight per fruit 360 g
  Fruit shape Elongate Bell (as in 'Lamuyo')
  Fruit set Scattered
  Number of locules 3–4
  Pedicel length Short (as in 'Yolo Wonder L')
  Pedicel shape Curved
  Pedicel thickness Thick (as in 'Yolo Wonder L')
SEED:
  Color Yellow
  Weight 9.7 g/1000 seeds
ANTHOCYANIN:
  Leaf Absent
  Fruit Absent
  Stem Absent
  Node Present Calyx Absent
Pedicel Absent
Seedling hypocotyl Present
DISEASE REACTION
Pepper mottle virus Susceptible
Potato Y virus Susceptible
Tobacco etch virus Susceptible
Tobacco mosaic virus Resistant Hybrid '0366' most closely resembles known variety 'Lamuyo' in terms of maturity, plant habit and fruit shape. It most closely resembles 'Yolo Wonder L' in terms of leaf color, leaf shape, immature fruit color and pungency. Its mature fruit closely resembles 'Ariane', ranging in color from 10R 5/12 to 10R 5/16.

What is claimed is:

1. Inbred bell pepper (*Capsicum annum L.*) seed designated 434 which has a dominant orange allele for fruit color and having ATCC accession No. 75975.

2. A pepper plant having a dominant orange allele for fruit color produced by growing the seed of claim 1.

3. The seed of the bell pepper plant of claim 2.

4. An F$_1$ hybrid pepper plant produced by a method comprising crossing an inbred pepper plant according to claim 2 with another different pepper plant having mature yellow-orange fruit, and harvesting and planting the seed obtained from such a cross.

5. Seed of the hybrid pepper plant according to claim 4.

6. An orange fruited bell pepper plant produced by the use of the seed claimed in claim 5.

7. Hybrid bell pepper seed designated NVH 3074 having ATCC accession No. 75141.

8. The pepper plant produced by growing the seed of claim 7.

9. Seed of the plant according to claim 8.

10. A method of using a first bell pepper (*Capsicum annum L.*) plant corresponding to the hybrid designated NVH 3074 accession number ATCC 75141 comprising crossing said first pepper plant with a second pepper plant wherein said second plant has yellow-orange fruit, harvesting and planting the seed obtained from such a cross, and obtaining a hybrid orange fruited plant.

11. The hybrid orange fruited plant obtained according to claim 10.

12. Seed of the plant according to claim 11.

* * * * *